United States Patent [19]
Jaffe et al.

[11] Patent Number: 5,361,063
[45] Date of Patent: * Nov. 1, 1994

[54] METHOD AND APPARATUS FOR SCHEDULING ACCESS TO A CSMA COMMUNICATION MEDIUM

[75] Inventors: David H. Jaffe, Belmont; Hoke S. Johnson III, Monte Sereno; Chris W. Eidler, Morgan Hill, all of Calif.

[73] Assignee: MTI Technology Corporation, Anaheim, Calif.

[ * ] Notice: The portion of the term of this patent subsequent to Dec. 29, 2009 has been disclaimed.

[21] Appl. No.: 964,204

[22] Filed: Oct. 21, 1992

Related U.S. Application Data

[60] Continuation of Ser. No. 617,218, Nov. 23, 1990, Pat. No. 5,175,537, which is a division of Ser. No. 501,663, Mar. 29, 1990, abandoned.

[51] Int. Cl.$^5$ .............................................. H04Q 5/00
[52] U.S. Cl. .................................. 340/825.5; 379/111; 370/85.2; 370/85.3; 370/85.6
[58] Field of Search ...................... 340/825.5; 379/111, 379/113, 131, 133, 137; 455/54.2, 58.2; 370/85.1, 85.2, 85.3, 85.4, 85.5, 85.6, 85.15, 94.1, 94.2, 60, 60.1, 13

[56] References Cited

U.S. PATENT DOCUMENTS

| | | | |
|---|---|---|---|
| 4,063,220 | 12/1977 | Metcalf et al. | 340/825.5 |
| 4,320,467 | 3/1982 | Glass | 340/825.5 |
| 4,412,326 | 10/1983 | Limb | 340/825.5 |
| 4,560,985 | 12/1985 | Strecker et al. | 340/825.5 |
| 4,613,729 | 9/1986 | Daisenberger | 379/113 |
| 4,704,724 | 11/1987 | Krishnan et al. | 379/113 |
| 4,733,303 | 3/1988 | Koshiishi | 358/257 |
| 4,805,170 | 2/1989 | Fergeson et al. | 340/825.5 |
| 4,926,641 | 5/1990 | Cidon et al. | 340/825.5 |
| 4,997,168 | 12/1990 | Courtois et al. | 370/85.3 |
| 5,012,510 | 4/1991 | Schaubs et al. | 379/92 |
| 5,042,027 | 8/1991 | Takase et al. | 370/54 |
| 5,067,074 | 11/1991 | Farel et al. | 370/13 |

FOREIGN PATENT DOCUMENTS

0241113 10/1987 European Pat. Off. .
3613898 10/1987 Germany .
59-204341 11/1984 Japan .

OTHER PUBLICATIONS

A. Arato et al., "A Local Area Network Architecture Tailored to Laboratory Environments", Interfaces in Computing, vol. 1, 1983, pp. 255-262.
I. Chlamtac et al., "Message-Based Priority Access to Local Networks", Computer Communications, vol. 3, No. 2, Apr. 1980, pp. 77-84.
I. Chlamtac et al., "BRAM: The Broadcast Recognizing Access Method", IEEE Transactions on Communications, vol. COM-27, No. 8, Aug. 1979, pp. 1183-1190.
G. S. Christensen et al., "Design and Analysis of the Access Protocol for Hyperchannel Networks", 3rd USA-Japan Computer Conference, 1978, pp. 86-93.
W. R. Franta et al., "Analysis of a Prioritized CSMA Protocol Based on Staggered Delays", Acta Informatica 13, 1980, pp. 299-324.
T. T. Lin et al., "A decentralized Conflict-Free Protocol, GBRAM for Large-Scale Local Networks", IEEE 1981, pp. 39-54.
N. Shacham et al., "A Protocol for Preferred Access in Packet-Switching Radio Networks", IEEE TOC, vol. COM-31, No. 2, Feb. 1983, pp. 253-259.
R. Signorile et al., "A Study of a Priority Protocol for PC Based Local Area Networks supporting Large File Transfers", 1987 Symposium on the Simulation of Computer Networks, Aug. 1987, pp. 123-127.

Primary Examiner—Donald J. Yusko
Assistant Examiner—Edwin C. Holloway III
Attorney, Agent, or Firm—Mark D. Rowland; Joseph M. Guiliano

[57] ABSTRACT

A scheduling mechanism is provided for controlling when the arbitration circuit of a node sharing a CSMA communication medium is to start CSMA arbitration for access to the communication medium once the node has a message ready for transmission, the scheduling mechanism delaying the arbitration circuit from seeking access if total transmission activity on the communication medium exceeds a total use threshold value and transmission activity of the node exceeds a local use threshold value, and otherwise permitting the arbitration circuit to seek access to the communication medium by arbitration in accordance with a priority value assigned to the node.

12 Claims, 9 Drawing Sheets

METHOD AND APPARATUS FOR SCHEDULING ACCESS TO A CSMA COMMUNICATION MEDIUM

This is a continuation of application Ser. No. 07/617,218, filed Nov. 23, 1990 entitled METHOD AND APPARATUS FOR SCHEDULING ACCESS TO A CSMA COMMUNICATION MEDIUM, now U.S. Pat. No. 5,175,537, which is a division of application Ser. No. 07/501,663, filed Mar. 29, 1990, now abandoned.

BACKGROUND OF THE INVENTION

The present invention relates to carrier sense multiple access (CSMA) protocols. In particular, the present invention relates to an improvement in scheduling transmissions within a CSMA protocol having a prioritized set of statically assigned time slots.

CSMA protocols generally can be considered as methods for distributing management of a communication medium among users of the medium. The medium with which CSMA protocols are concerned in a single-carrier communication medium, such as a co-axial communication bus in a computer network or system or a transmission channel in a satellite network, in which an arbitration mechanism must be embedded in the same carrier used to convey data.

Many variants of CSMA protocols are known. In some of these variants, prioritized arbitration is accomplished by assigning each node sharing the communication medium a unique time slot during which the node may initiate transmission if no other node having a higher priority (i.e., an earlier time slot) has already begun a transmission. The set of time slots for all nodes is synchronized to within one propagation time interval with the trailing edge of the carrier signal that follows the end of a transmission on the communications medium.

Where time slots are assigned statically (e.g., the time delay for each node of a network is set at the time of installation and is not changed thereafter), nodes having low priority may experience long delays in obtaining access to the communication medium, particularly during periods of heavy traffic.

To place an upper boundary on transmission delays for all messages originating at any node, "fair" CSMA protocols have been developed in which assigned priorities are varied such that all nodes awaiting access at a given instant are allowed to access the communication medium once before any node is given a second chance. For a discussion of such a "fair" protocol, see "BRAM: The Broadcast Recognizing Access Method," Chlamtac, I., Franta, W. R., and Levin, K. D., IEEE Transactions On Communications, Vol. Com-27, No. 8, August 1979, pp. 1183–1190; and "Message-based priority access to local networks," Chlamtac, I. and Franta, W. R., Computer Communications, Vol. 3, No. 2, April 1980, pp. 77–84.

In at least certain network configurations, such as a computer network including one or more server nodes, a fair CSMA protocol does not necessarily provide good system throughput. This is because an application may require that a server node have high priority access to the communication medium to handle a large number of data requests.

For example, where a server node comprises a mass storage subsystem that handles the mass storage needs of several other nodes (referred to hereafter as "served nodes"), the server node is likely to be a bottleneck in the network if it is limited to seeking access to the network bus on a fair basis with each of the served nodes. In general, to avoid a bottleneck situation, the server node should be allowed a share of the bus bandwidth at least equal to the sum of the bandwidth shares of the served nodes (assuming that the mass storage subsystem is capable of operating at such a rate). In a prioritized CSMA protocol, this level of system performance (i.e., share of bus bandwidth) can only be guaranteed if the server node is statically assigned the highest priority for bus access. Otherwise, the performance level of the subsystem, as well as that of the entire system, may be limited to less than its potential capability. Nodes having priority higher than that of the mass storage subsystem node may capture a share of bus bandwidth that does not leave sufficient bandwidth available for the mass storage subsystem to perform up to its potential maximum throughput capacity.

On the other hand, a server node having statically-assigned high priority access also may, in some applications, cause system throughput to be degraded because the server node uses a large share of the communication medium bandwidth at a time when other nodes need to transmit. System throughput in such a case would be improved if the share of bandwidth used by the server node could be dynamically adjusted based on attributes of particular applications.

It may also occur in a network that a server node is capable of transmitting data at a faster rate than a receiving node can successfully receive the data. System throughput suffers if, as a result of such difference in data handling capacities among nodes, a serving node must re-transmit data that a slower node was incapable of receiving successfully. This problem can be avoided by providing a means for the server node to lower its effective transmission rate when transmitting to slower nodes.

It would thus be desirable within a CSMA protocol to permit a node to dynamically adjust its share of transmission time on the communication medium to improve system throughput in different network applications.

It would further be desirable to be able to implement such an adjustable control mechanism in a manner that would allow a node to vary its share of the communication medium without violating priority arbitration schemes incorporated in CSMA protocols, such that the adjustable control mechanism could be utilized by a device in networks having various types of CSMA protocols.

It would also be desirable to be able to provide a mechanism for selectively reducing the transmission rate of transmissions to nodes having low data handling capacity.

SUMMARY OF THE INVENTION

It is an object of the present invention to provide within certain types of prioritized CSMA protocols a mechanism for allocating an adjustable share of transmission bandwidth to particular nodes.

It is a further object of the present invention to provide an arbitration circuit incorporating a configurable scheduling mechanism which can be implemented with any CSMA protocol of the type having at least one set of prioritized arbitration time slots.

It is an additional object of the present invention to provide a mechanism for determining a receiving node's data transfer rate and for generating for each receiving node a scaled speed estimate based on this determination.

It is also an object of the present invention to provide a mechanism for scheduling a delay between transmissions to a node to reduce the rate at which data is transmitted to a slower receiving node. The term "per-node throttling" is used herein to refer to the function of such a mechanism.

In accordance with the present invention, a dynamic scheduling mechanism having configurable parameters is provided for controlling when the arbitration circuit of a node sharing a CSMA communication medium is to seek access to the communication medium once the node has a message ready for transmission, the scheduling mechanism delaying the arbitration circuit from seeking access if (1) total transmission activity on the communication medium exceeds a total use threshold value and (2) transmission activity of the node exceeds a local use threshold value, and otherwise permitting the arbitration circuit to seek access to the communication medium by arbitration in accordance with a priority value assigned to the node.

There is further provided a dynamic per-node throttling mechanism for delaying sequential transmissions from a transmitting node to any receiving node in the network having a slower data transfer rate than the transmitting node. The relative speed of a receiving node is determined by the frequency with which negative acknowledgment responses have been received from that node in the past. An algorithm is provided for introducing dynamically variable and node-specific delay periods between sequential transmissions to slower nodes based on the determined relative speed of each individual receiving node.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1A:
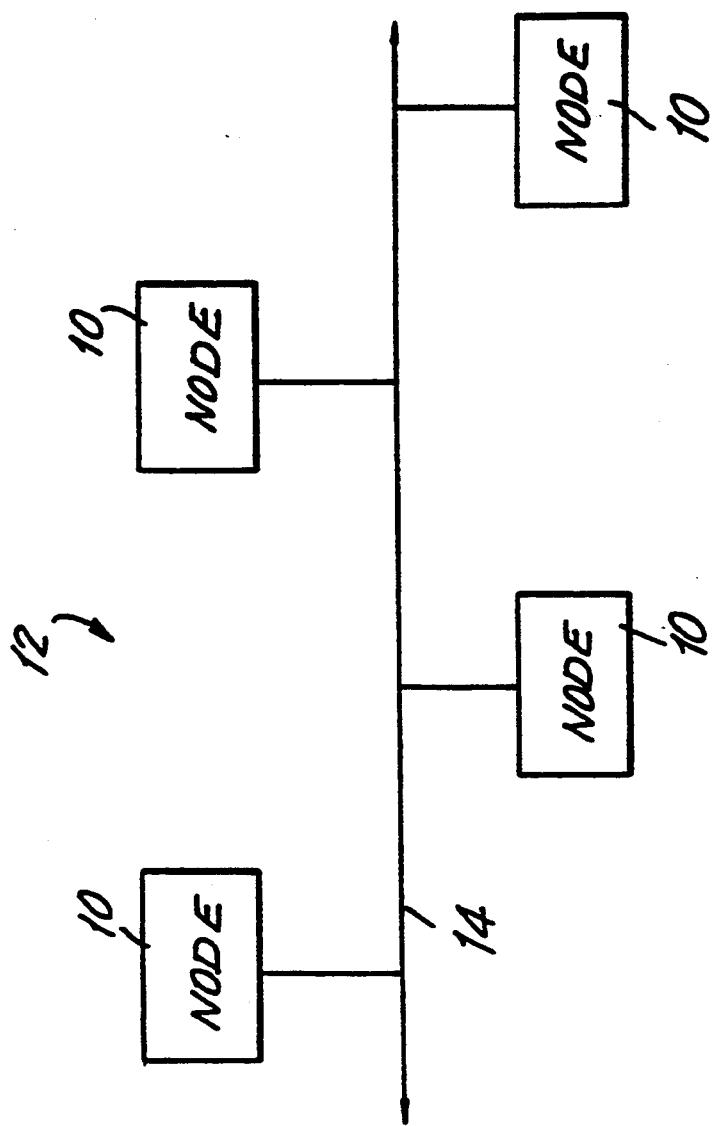
FIGS. 1A and 1B illustrate, respectively, a computer network having a plurality of nodes, and a schematic diagram of an arbitration system for a node on a CSMA protocol communication bus including scheduling mechanisms in accordance with the present invention.

Referring to FIG. 1A, the present invention particularly concerns prioritized CSMA protocols in which a set of time slots are statically assigned to the nodes 10 of a network 12 sharing a common communication medium 14. Each slot of the set may be assigned to one and only one node, or may be assigned to a plurality of nodes. A node may even be assigned or assign itself to more than one time slot in the set if it has a particularly great need for time on the medium. The set of time slots provides priority access control for nodes wishing to transmit when the communication medium is busy. This is typically accomplished in conventional collision avoidance type CSMA protocols as follows.

Each transmission on the communication medium is accompanied by a carrier signal. At the end of a transmission on the medium, the carrier signal ceases and the medium enters an idle state for a fixed period of time. During this fixed period of time, only a node responding to the previous message is allowed to transmit. Thus interference with a required response message (e.g., an ACK or NAK message) is prevented. Following the fixed delay period, a time slot period begins. During this period each node has one or more time slots in which it may capture the communication medium without interference from other nodes, thus establishing a priority system for capture of the communication medium. A node wishing to transmit a message waits only until its time slot occurs, at which time it can freely access the communication medium without interference if the medium is idle. The time slots assigned to nodes in the network depend on the priority the nodes are to be given—the higher the priority, the closer the time slot is to the beginning of the time slot period.

In a network in which such a prioritized CSMA protocol is used to control access to a common communication medium, each node generally includes an arbitration circuit that monitors transmission activity on the communication medium and determines when the node is allowed to access the medium to transmit a message. This determination is made in accordance with the rules of the CSMA protocol, and is typically accomplished using hardware logic and associated circuitry which has been programmed according to the prioritizing function of the CSMA protocol.

Figure 1B:
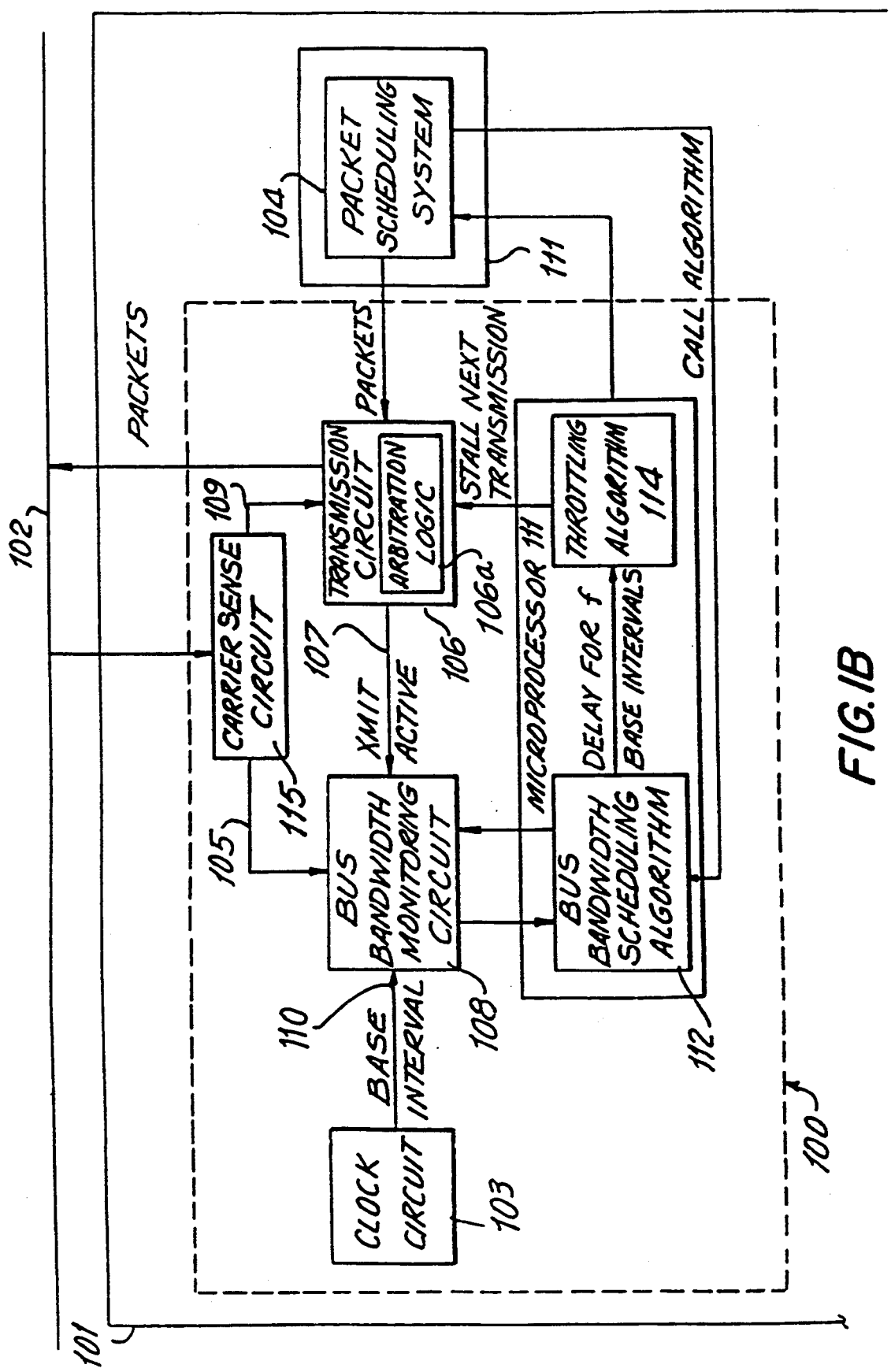

FIG. 1B illustrates a configurable arbitration circuit 100 in accordance with the principles of the present invention. Arbitration circuit 100 is shown as part of a node 101 in a local area network or a distributed computing system, and is connected to a communication bus 102 of the network or system. Communication bus 102 may be realized using any one of various known technologies such as fiber optics, coaxial cable or microwave channel. Bus 102 may comprise a single bit-serial line. In a preferred embodiment, arbitration circuit 100 is implemented as part of a bus interface unit for connecting a node to a serial communication path of a packet-switching type network.

Messages to be transmitted on bus 102 are provided to arbitration circuit 100 by a packet scheduling system 104 that assembles the messages into packets. Packet scheduling system 104 is controlled by a processor 111. The packets are provided to transmission circuit 106, which includes arbitration logic circuitry 106a for determining, in accordance with a lower level of the CSMA protocol, when node 101 may take control of bus 102 to initiate a transmission. Carrier sense circuitry 115 detects the state of bus 102 (busy or idle) by detecting the presence or absence of a carrier signal on the bus and generates carrier detect signals 105 and 109. The arbitration logic circuitry 106a, in response to transmission circuit 106 receiving a packet from packet scheduling system 104 ready for transmission, checks the carrier sense circuitry 115 to determine if a carrier is present on bus 102. If a carrier is present, signifying that another node sharing bus 102 has control of the bus, the arbitration logic circuitry 106a waits for the carrier sense circuitry 115 to detect the falling edge of the carrier signal.

When a falling edge is detected, the arbitration logic circuitry 106a enters a first timed waiting state. This waiting state allows a receiving node in the network time to send an acknowledgement message in response to the termination of the last transmitted message without having to arbitrate for control of bus 102. The duration of this waiting state is typically equal to the amount of time required for a signal to propagate from one end of bus 102 to the other, plus the amount of time required to detect a carrier. The waiting state also allows a node that has access to bus 102 to continue to use it in a series of transmissions.

When the first timed waiting period elapses, the arbitration logic circuitry 106a then enters a second timed waiting state during which it checks the carrier sense circuitry 115 for the presence of a carrier signal on bus 102. The duration of the second waiting period is determined by the priority value assigned to the node. The node must wait this second period to allow nodes having higher priority values (and thus shorter waiting periods) an opportunity to initiate a transmission. The nodes are each given one or more limited time slots in which to initiate transmission, the duration of each time slot typically being the same as that of the first waiting period.

If bus 102 becomes active during the second waiting period (signifying that a node of higher priority has won control of the bus), the arbitration logic circuitry 106a again awaits the end of the transmission and repeats the first and second timed waiting periods. If bus 102 remains idle throughout the second waiting period, the arbitration logic circuitry 106a may win control of the bus by initiating a transmission during its assigned time slot. Transmission circuit 106 preferably includes programmable clock and counter circuits for measuring the first and second waiting periods. These circuits are programmed in accordance with the physical properties of the network (e.g., distance between nodes, number of nodes, etc.) and the assigned priority value of node 101. The counter circuit, for example, may be a modulo counter that is programmed to repeatedly count down the necessary waiting periods. The counter is reset each time a falling carrier edge is detected. Thus, whenever the node has a packet ready for transmission, the node waits until the modulo counter next reaches its terminal count (e.g., zero) before initiating a transmission.

In conventional modes of network communication, successful receipt of a message is normally acknowledged by the receiving node immediately after the message transmission is completed. This acknowledgement typically takes the form of an acknowledgement message (ACK) which is transmitted by the receiving node to the transmitting node during a fixed period of time following the end of the previous transmission. A negative acknowledgement response (NAK) is transmitted by the receiving node to the transmitting node instead if the message was successfully transmitted to the intended receiving node, but that node was too busy to properly buffer the message. If a proper acknowledgement (ACK or NAK) is not received within this fixed period (e.g., because the intended receiving node did not receive the transmission), the transmitting node considers the transmission to have failed.

The transmitting node, upon receiving either no acknowledging response, or an acknowledgement response indicating that the message packet was properly received but could not be handled by the receiving node (e.g., a NAK), will attempt to retransmit the message. This acknowledgement process and the rescheduling of transmitted messages is accomplished by the packet scheduling system 104 of the node.

When transmitting a message, transmission circuit 106 provides a XMIT ACTIVE signal 107 to bus bandwidth monitoring circuit 108 indicating that the node is transmitting. Bus bandwidth monitoring circuit 108 receives from carrier sense circuitry 115 a carrier detect signal 105 indicating the presence or absence of transmission activity on bus 102. Bus bandwidth monitoring circuit 108 and transmission circuit 106 may use the same carrier sense circuitry 115 as shown in FIG. 1B.

The function of bus bandwidth monitoring circuit 108 is to generate (1) a measure of the amount of the bandwidth of bus 102 that is used by all nodes sharing the bus (total bus bandwidth use), and (2) a measure of the amount of bandwidth used by the node 101 which includes arbitration circuit 100 (local bus bandwidth use). The first measure is taken by sampling bus 102 at a constant rate for the presence of a carrier signal. The second measure is taken by sampling XMIT ACTIVE signal 107, preferably at the same constant rate.

A synchronous base interval signal 110 is provided by clock circuit 103 to bus bandwidth monitoring circuit 108 to clock the sampling functions. The sampling rate can be chosen as desired. For example, a sampling rate may be defined such that the time between samples is equal to the period of a time slot assigned to a node sharing bus 102 (which is based on propagation delay across bus 102 and the amount of time required to detect a carrier). The measures of total bus bandwidth use and local bus bandwidth use generated by bus bandwidth monitoring circuit 108 are provided to bus bandwidth scheduling algorithm 112. Bus bandwidth scheduling algorithm 112, which is preferably implemented using a subroutine executed by processor 111, controls the rate at which transmission circuit 106 arbitrates for control of bus 102 in response to the scheduling of packets by packet scheduling system 104. Bus bandwidth scheduling algorithm 112 may also be implemented using other types of conventional logic circuitry, such as a programmable state machine logic circuit.

Scheduling algorithm 112 may exercise control over transmission circuit 106 in any one of several ways. For example, scheduling algorithm 112 may be capable of temporarily disabling the transmission circuit 106 to prevent it from transmitting a packet scheduled by packet scheduling system 104, or it may be capable of temporarily preventing packets from being provided to transmission circuit 106 by package scheduling system 104.

Bus bandwidth scheduling algorithm 112 operates to reduce the rate at which node 101 transmits packets when total activity on the bus exceeds a first threshold percentage of the available bandwidth of bus 102 and the share of bus bandwidth used by node 101 exceeds a second threshold percentage of the available bandwidth of bus 102. Pertinent values and parameters are labeled in FIG. 2, which illustrates a bandwidth gauge 200 of bus 102.

Figure 2:
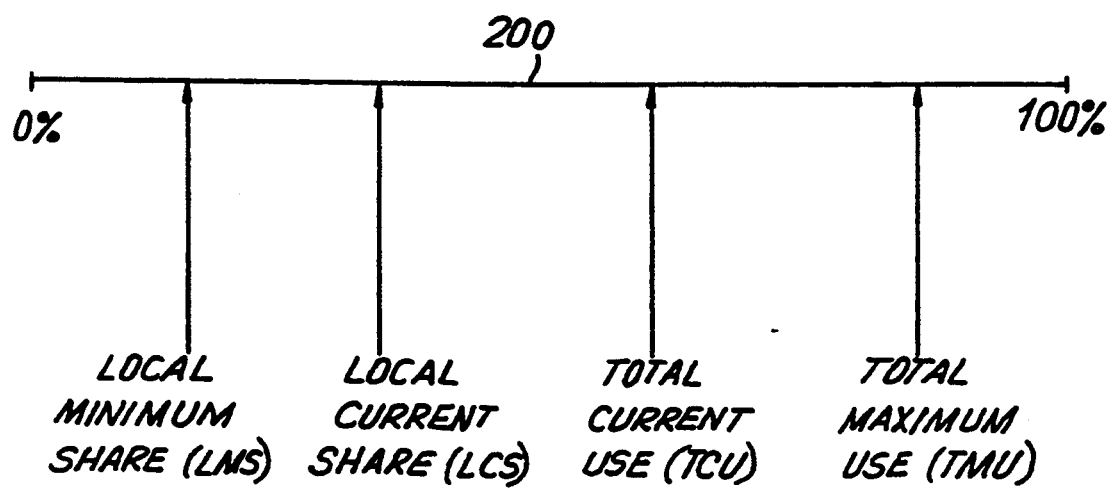
FIG. 2 is a diagram of a gauge of the bandwidth of a shared communication medium, such as the communication bus of FIG. 1.

Referring to FIG. 2, total transmission activity on bus 102 is indicated by Total Current Use (TCU). The above-stated first threshold percentage of available bandwidth is indicated by Total Maximum Use (TMU). The share of available bus bandwidth used by node 101 for transmissions is indicated by Local Current Share (LCS), and the above-stated second threshold percentage is indicated by Local Minimum Share (LMS).

Using these labels, the function of bus scheduling algorithm 112 can be stated as follows: if total transmission activity on bus 102 (TCU) exceeds a maximum threshold percentage (TMU) of available bandwidth on bus 102, which may, for example, be 80% (i.e., the bus is busy 80% of the time), reflecting that overall demand for use of the bus is high, and if node 101 has a share of transmission activity on the bus (LCS) exceeding a minimum threshold value (LMS), then bus bandwidth scheduling algorithm 112 introduces a delay into the rate at which node 101 arbitrates for access to the bus to reduce the total transmission activity (TCU) value to (or below) the maximum threshold percentage (TMU) and/or to reduce the share of node 101 (LCS) to (or below) the minimum threshold (LMS).

The threshold values of Total Maximum Use (TMU) and Local Minimum Share (LMS) are dependent on the particular configuration of the network, and the particular application being run on the network. These threshold values can be varied from one network to another, and from one application to another, as appropriate to achieve optimum system throughput. For any particular configuration and application the appropriate threshold values can be determined empirically.

Figure 3:
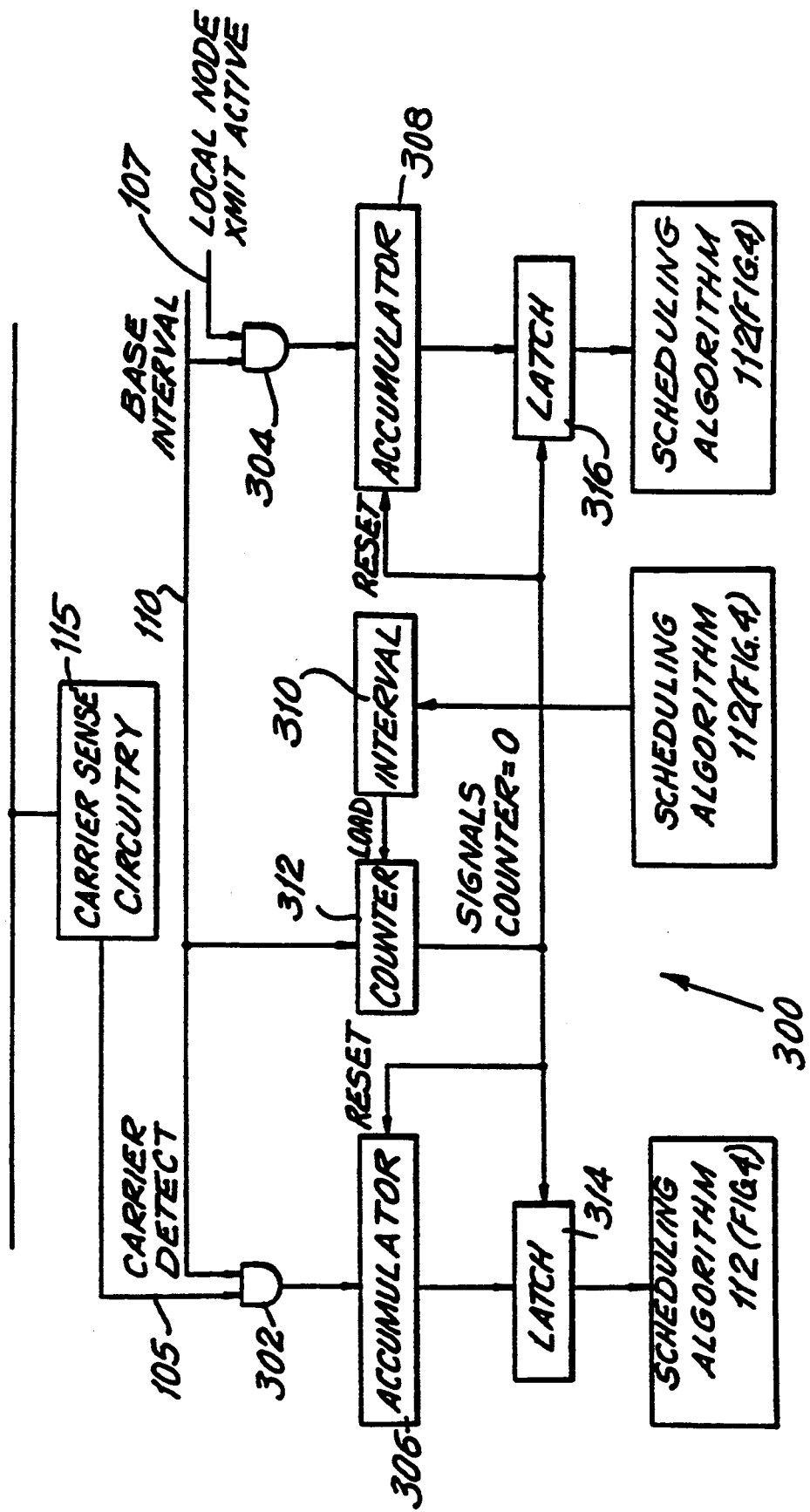
FIG. 3 is a schematic diagram of an embodiment of a circuit for use in implementing the configurable bandwidth monitoring mechanism of FIG. 1.
Figure 4:
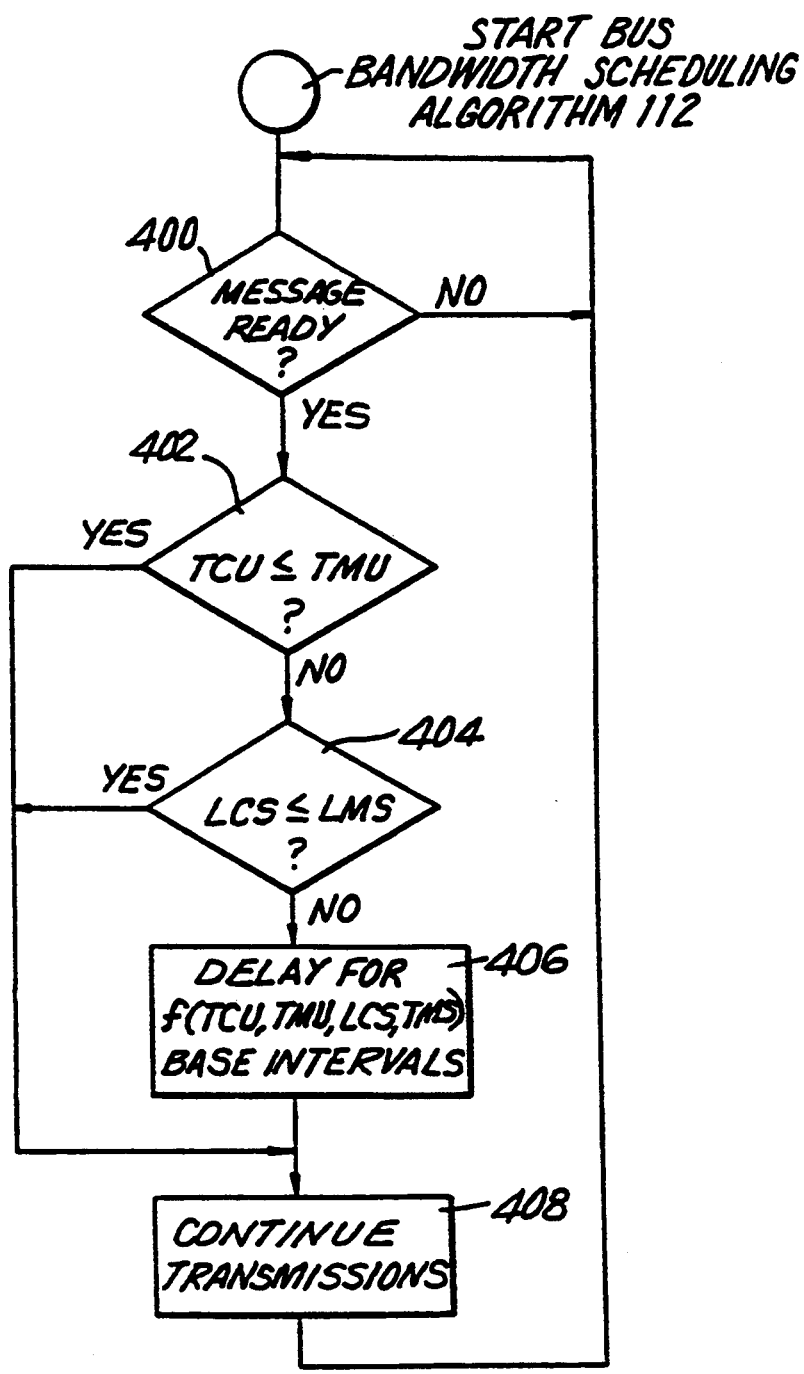
FIG. 4 is a diagram of a flow chart showing the steps of an exemplary implementation of the method of the configurable bandwidth scheduling mechanism of the present invention.

The operation of an exemplary embodiment of bus bandwidth scheduling algorithm 112 is illustrated by FIGS. 3 and 4. FIG. 3 shows a circuit 300 incorporated in bus bandwidth monitoring circuit 108 for generating measures of total and local bus bandwidth use. Circuit 300 includes AND logic gates 302 and 304 which respectively sample carrier detect signal 105 and XMIT ACTIVE signal 107 in response to each clock cycle of synchronous base interval signal 110. The output of AND gate 302 is coupled to the clock input of accumulator 306, which is incremented once for each time a carrier signal is detected when sampled by AND gate 302.

Likewise, the output of AND gate 304 is coupled to the clock input of accumulator 308, which is incremented once for each time node 101 is transmitting when sampled by AND gate 304. Accumulators 306 and 308 are reset at a regular interval defined by a count value stored in interval register 310 by scheduling algorithm 112. This interval count value is, in turn, loaded into counter circuit 312, which decrements the value once for each clock cycle of base interval signal 110. When counter circuit 312 reaches zero, accumulators 306 and 308 are loaded respectively into latch registers 314 and 316, and the accumulators are reset to begin a new count.

The values stored in latch registers 314 and 316 provide scheduling algorithm 112 with respective measures of total transmission activity on bus 102 and local transmission activity of node 101 over an interval defined by the scheduling algorithm. The values are updated every interval, such that the measures are kept current. In performing its control function, the algorithm uses the value of latch register 314 as the previously described parameter Total Current Use (TCU), and the value of latch register 316 as the previously described parameter Local Current Share (LCS). A flow chart of an exemplary subroutine for implementing the control function of scheduling algorithm 112 using processor 111 is shown in FIG. 4.

Referring to FIG. 4, the subroutine is activated by processor 111 when packet scheduling system 104 has a packet ready for transmission (step 400). As part of packet scheduling system 104, processor 111 may maintain a queue of identifiers corresponding to ready packets. If a packet is ready, as indicated by an identifier corresponding to the packet being placed in the queue, processor 111 reads the value of latch register 314 and compares the value to the programmed threshold value Total Maximum Use (TMU). If the Total Current Use (TCU) value of latch register 314 is less than or equal to the Total Maximum Use threshold value (TMU), processor 111 enables transmission circuit 106 to arbitrate for control of bus 102 to transmit the ready packet (or, depending on the implementation, allows the ready packet to be given to transmission circuit 106 by packet scheduling system 104). Steps 402 and 408.

Otherwise, processor 111 reaches another decision point (step 404) in which it reads the value of latch register 316 and compares the value to the programmed Local Minimum Share threshold value (LMS). If the Local Current Share value (LCS) of latch register 316 is less than or equal to the Local Minimum Share threshold value (LMS), the algorithm allows the ready packet to be transmitted. Otherwise, the algorithm delays the packet (step 406) for a period of time (e.g., a certain number of cycles of base interval signal 110) before allowing the ready packet to be transmitted.

The delay period is defined by a function (f), which preferably provides a delay value that reduces node 101 bus bandwidth use such that either (1) the Local Current Share (LCS) value is reduced to (or below) the Local Minimum Share (LMS) threshold value, or (2) the Total Current Use (TCU) value is reduced below the Total Maximum Use (TMU) threshold value. This function may be implemented in various ways. For example, function (f) may comprise an indexing function for pointing to a particular delay value in a table of various empirically determined delay values. Alternatively, function (f) may comprise a formula for calculating the delay value, such as the following:

f(TCU, TMU, LCS, LMS)=the lesser of
(LCS-LMS) and (TCU-TMU) [in cycles of base
interval signal 110]

Scheduling algorithm 112 may alternatively calculate a measure of free time on bus 102 (e.g., by subtracting the Total Current Use value (TCU) of latch register 314 from the value of interval register 310), and use the value of bus free time as a parameter (instead of using its complement).

As can be seen from the above-described embodiments of bus bandwidth scheduling algorithm 112, the control function of the algorithm can be varied (e.g., by varying the threshold parameters) to vary the share of bus bandwidth controlled by arbitration circuit 100.

As shown in FIG. 1B, the present invention further includes a per-node throttling algorithm 114 executed by processor 111 which restrains (or throttles) the rate at which node 101 may transmit to any particular receiving node sharing bus 102. Repeated high speed transmissions to a single node may result in packets being received by the node at a greater rate than they can be buffered and processed, such that the packets are discarded by the receiving node and must be retransmitted.

Retransmission of a packet wastes bandwidth on bus 102. This wasted bandwidth can be reduced by requiring node 101 to limit the rate at which it transmits packets to a slower receiving node. Throttling algorithm 114 accomplishes this limiting function by introducing a delay between sequential transmissions to the slower receiving node. More particularly, throttling algorithm 114 monitors NAKs received by node 101 and computes, for each receiving node in the network, a NAK rate per packet transmitted by node 101. Throttling algorithm 114 requires that a certain minimum delay period elapse between transmissions to a particular node if the past performance of that node reflects a per-packet NAK rate that exceeds a threshold value. The threshold value can be varied from network to network, from application to application and from node to node as appropriate to optimize system throughput in each case.

Preferably, where a minimum delay is imposed on transmissions to a particular node, the duration of the minimum delay is a computed value based on the observed per-packet NAK rate for that node. Although the data handling capabilities of particular nodes may be known prior to the beginning of an application, these capabilities will normally vary during operation, such that optimum system performance is more likely to be achieved by detecting such variations "on the fly" and adjusting the length of any minimum delay imposed to take into account the magnitude of the variations. For this purpose, throttling algorithm 114 preferably uses the per-packet NAK rate as a scaled estimate of the current data handling capability, or speed, of each receiving node, not only for determining whether or not to delay transmissions to the receiving node, but also to determine the duration of the delay.

An example of an embodiment of throttling algorithm 114 is described below. For purposes of illustration, the exemplary embodiment of throttling algorithm 114 is described in the context of a packet-switching type network in which node 101 is a server node for a plurality of other nodes (served nodes). A flow chart of the algorithm is shown in FIGS. 5A–5C.

Figure 5A:
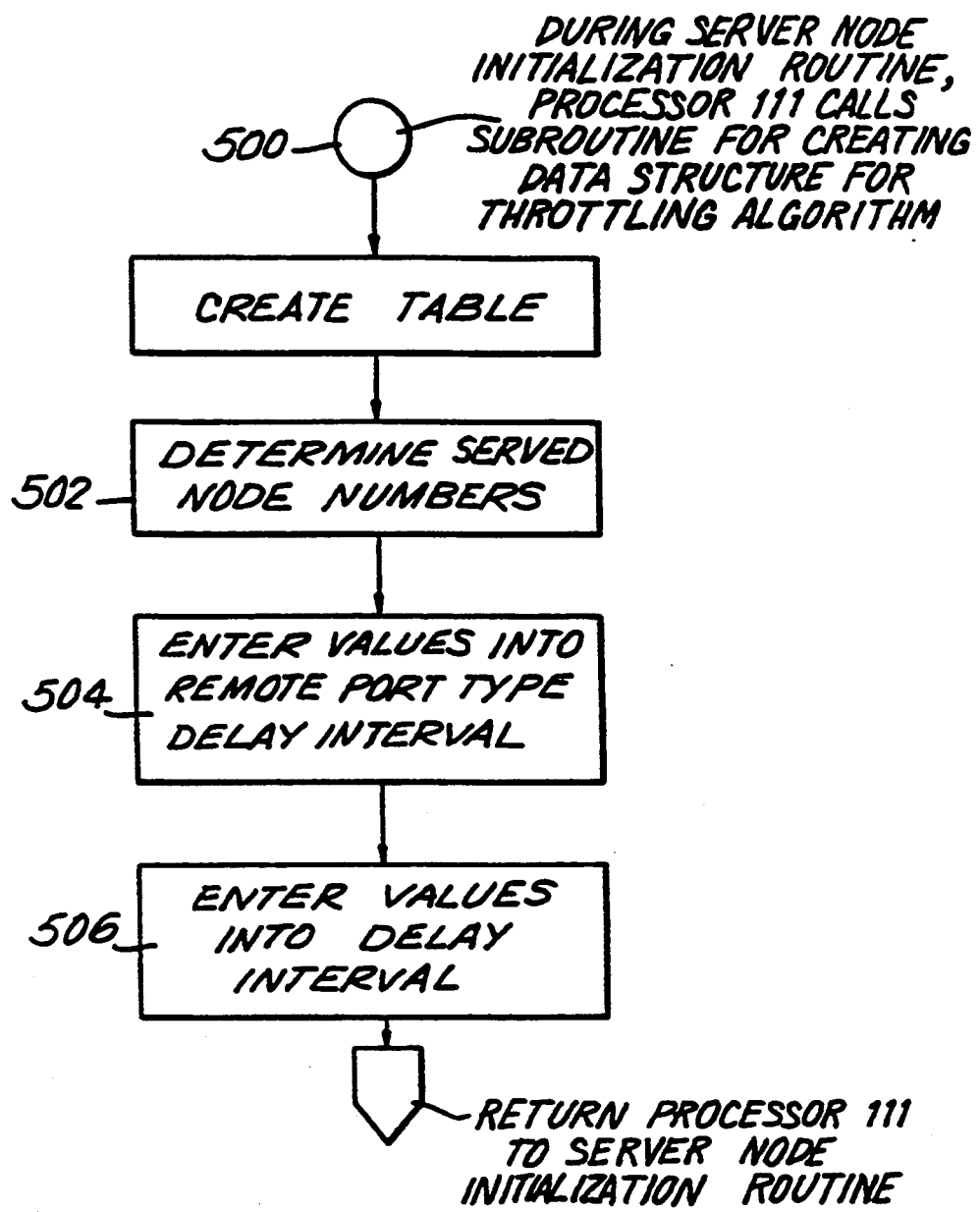
FIGS. 5A–5C are diagrams of a flow chart showing the steps of an exemplary implementation of the method of the per-node throttling mechanism of the present invention.
Figure 5B:
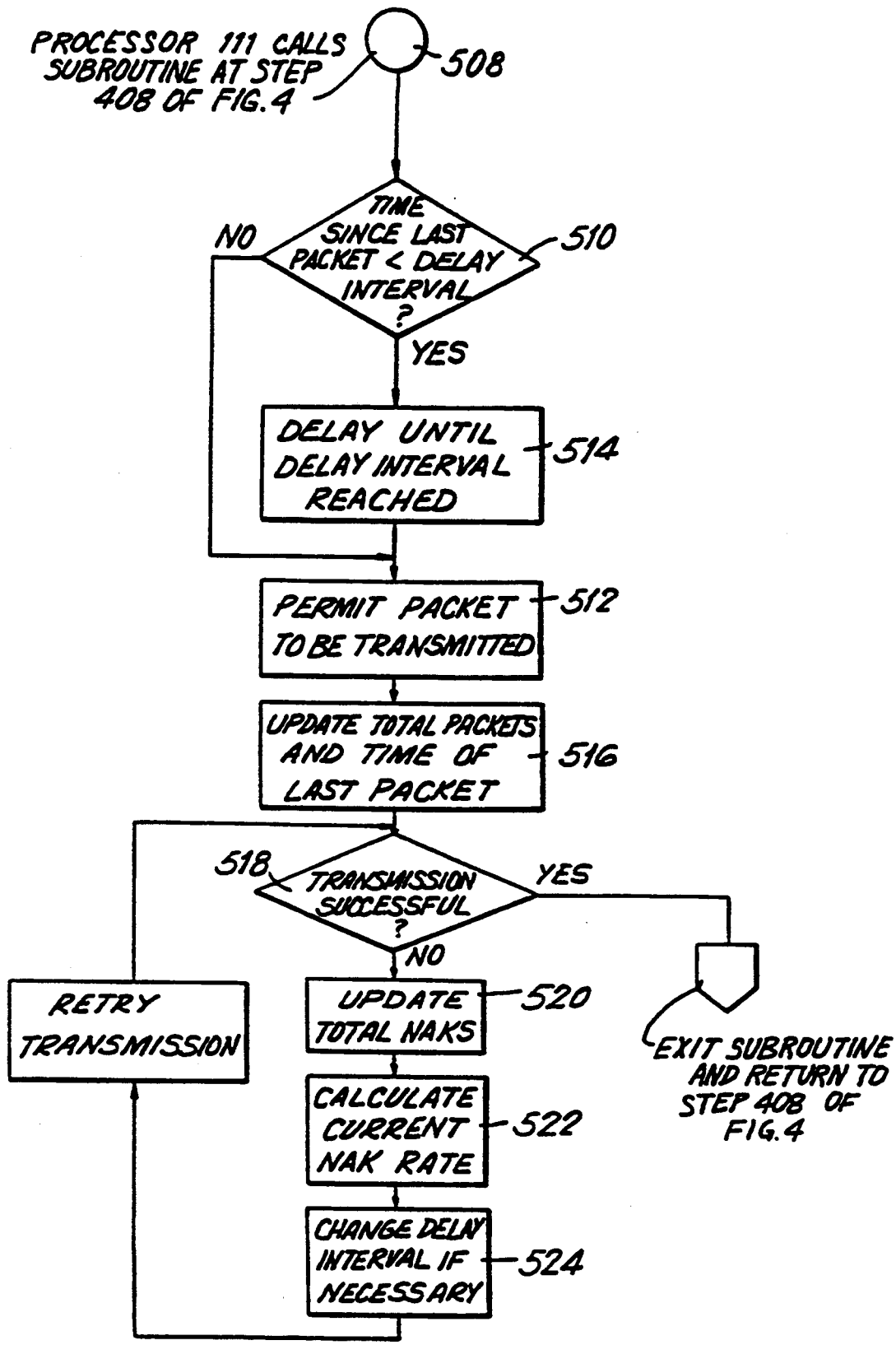
Figure 5C:
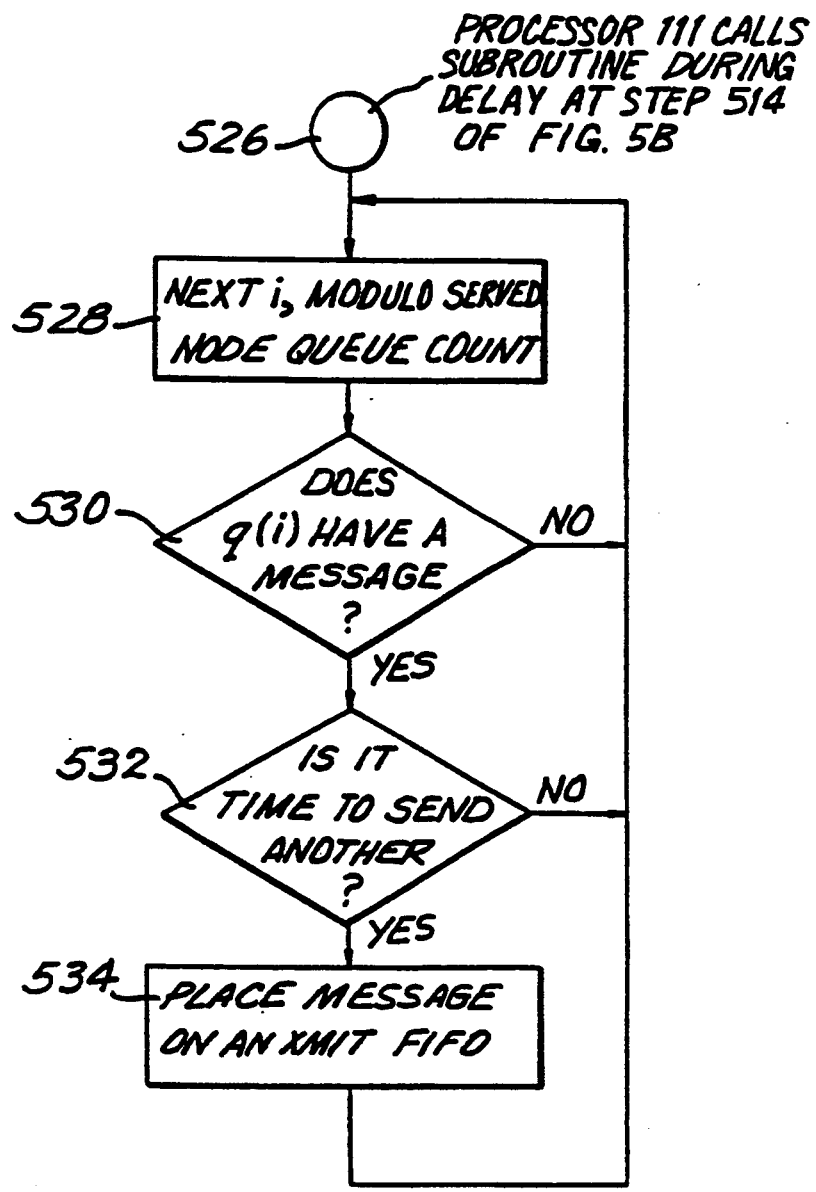
Figure 6:
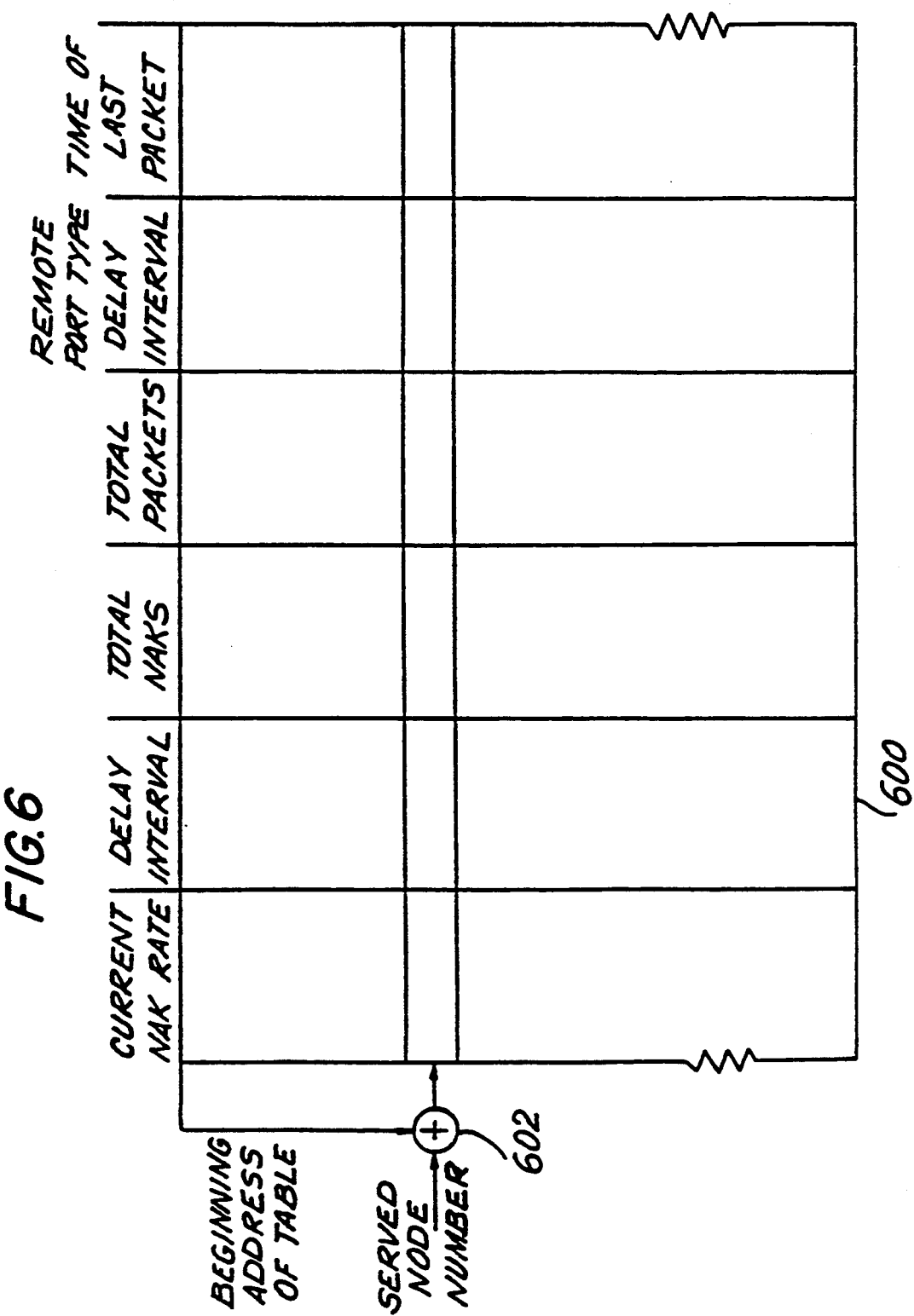
FIG. 6 is a diagram of a table reflecting various values and parameters for the per-node throttling mechanism of the present invention.

The steps of throttling algorithm 114 shown in FIGS. 5A–5C are preferably implemented using subroutines executed by processor 111. First, during initialization of the server node, a subroutine (500 of FIG. 5A) is called to create a data structure in the memory of processor 111. An illustrative diagram of such a data structure 600 is shown in FIG. 6. The data structure includes columns for entering the following information for each served node on the network with which node 101 must communicate: CURRENT NAK RATE, DELAY INTERVAL, TOTAL NAKS, TOTAL PACKETS, REMOTE PORT TYPE DELAY INTERVAL and TIME OF LAST PACKET.

Each row of the data structure represents information for a different served node. The rows are identified by numbers assigned to the served nodes by processor 111. Step 502 of FIG. 5A. The served node numbers represent the offset in memory of each corresponding row from the top of data structure 600. Processor 111 addresses the various rows of the data structure by combining the respective served node number with the beginning memory address of the data structure in address pointer 602. Based on parameter values input by the operator or some other source at initialization, processor 111 enters into the REMOTE PORT TYPE DELAY INTERVAL column a delay value for each served node. Step 504. Processor 111 also enters this value into the DELAY VALUE column as an initial value. Step 506.

Preferably, when the server node is connected, the node exchanges information with served nodes concerning the type of ports those served nodes are using, and the operator chooses initial delay values for the network nodes depending on known limitations in the data transfer capacities of the port types for those nodes. For some or all nodes, the operator may choose to begin with no initial delay. The operator may also choose to set the same initial delay for transmissions to all nodes.

During run time, the delay values in the DELAY INTERVAL column are used by processor 111 to set the minimum delay between transmissions to each node. Processor 111 maintains a queue in which it identifies packets that are ready for transmission and the number of the served node to receive the packets. When scheduling algorithm 112 has determined that node 101 may transmit (step 408), scheduling algorithm 112 calls subroutine 508 of throttling algorithm 114. Subroutine 508 checks the entry in the DELAY INTERVAL column corresponding to the served node that is to receive the next packet and determines whether that value (if non-zero) is greater than the time that has elapsed since the last packet was sent to that served node. Step 510. The time of the last transmission is found in the TIME OF LAST PACKET column of data structure 600.

If the time since the last transmission to that served node is equal to or exceeds the value of DELAY INTERVAL, throttling algorithm 114 permits the transmission to take place without further delay. Step 512. Otherwise, processor 111 delays the transmission until the delay interval is reached. Step 514.

After the transmission of a packet, processor 111 updates the value of the entries in the TOTAL PACKETS and TIME OF LAST PACKET columns for the served node that was sent the packet. Step 516. The entry reflects the total number of packets sent to a particular served node. Processor 111 then awaits a response from the served node. If the served node acknowledges successful receipt, the processor exits the subroutine. Step 518. If a NAK is received from the served node, processor 111 updates the value of the entry in the TOTAL NAKS column for that served node. Step 520. Processor 111 updates the TOTAL NAKS column for each NAK received. Processor 111 also calculates a CURRENT NAK RATE value for the served node by dividing the value of the entry in the TOTAL NAKS column by the value of the entry in the TOTAL PACKETS column, and determines whether the value of DELAY INTERVAL should be changed. Steps 522 and 524.

Processor 111 preferably increases the value of DELAY INTERVAL for a served node if the value of CURRENT NAK RATE for that served node increases. This may be accomplished in various ways. The particular method chosen is implementation specific. As one example, a look-up table may be provided according to which different DELAY INTERVAL values are specified for each served node for different values, or ranges of values, of CURRENT NAK RATE. Each time the CURRENT NAK RATE for a served node increases, processor 111 checks the look-up table to determine if the new value corresponds to a new DELAY INTERVAL value. In this manner, it may be provided that the DELAY INTERVAL value remains at zero until an initial non-zero threshold value for CURRENT NAK RATE is exceeded. Alternatively, processor 111 may increment the DELAY INTERVAL value by a fixed number each time the CURRENT NAK RATE increases, or another function may be defined for calculating the value of DELAY INTERVAL based on the value of CURRENT NAK RATE.

Likewise, the value of DELAY INTERVAL for a particular node may be decreased to reflect downward changes in the CURRENT NAK RATE value. Processor 111 may also check at this time, or on a periodic basis, for abnormally high values of CURRENT NAK RATE indicative of a malfunctioning remote port.

It is a known practice in network communication for a server node to schedule transmissions to various receiving nodes in an interleaved manner to provide a balanced throughput. Throttling algorithm 114 may take advantage of this technique while awaiting a delay interval for a particular node to elapse by transmitting packets to other nodes during the interval. FIG. 5C illustrates a subroutine 526 that may be called by processor 111 to accomplish this.

Processor 111 maintains a modulo-n served node queue counter, n being equal to the number of nodes served by the mass storage subsystem. Each served node is represented by a different value of the counter. These values correspond to the served node numbers that identify the rows of data structure 600. When a packet ready for transmission by node 101 is delayed by throttling algorithm 114, the value of the counter is set equal to the next modulo-n value following the number of the served node that is to receive the delayed packet. Step 528. Processor 111 checks a queue of other packets ready for transmission to determine if any are destined for the served node indicated by the modulo-n counter. Step 530. Such a queue is preferably maintained for each served node. If a packet is ready, processor 111 then determines whether for that particular served node there is a need to delay transmission of the ready packet to prevent the bandwidth capacity of the served node from being exceeded. Step 532. If not, processor 111 causes the packet to be transmitted, and determines if another packet is ready for transmission to that served node (thus allowing consecutive packets to be transmitted to a particularly fast port). Step 534. If no packet is ready for transmission to the served node the count is incremented and the queue for the next served node is checked for a ready packet. This process repeats until the delay interval of the initial packet times out.

Thus a novel method and apparatus for scheduling transmissions within a CSMA protocol communication medium have been described. One skilled in the art will appreciate that the present invention can be practiced by other than the described embodiments, and in particular may be incorporated in circuits other than the described mass storage subsystem. The described embodiment is presented for purposes of illustration and not of limitation, and the present invention is limited only by the claims which follow.

What is claimed is:

1. In a network including a plurality of nodes, a method implemented within a first network node for limiting the rate at which the first network node transmits sequential transmissions to a second node in the network which also receives transmissions from other network nodes, the method comprising the steps of:

determining a dynamic estimate of the data handling capability of the second node from past transmissions between the first and second nodes, independently of any source of information directly indicative of the total data handling load on the second node caused by transmissions from the first and other network nodes;

defining a minimum delay period for sequential transmissions to the second node as a function of the determined estimate of the data handling capability of the second node; and delaying a scheduled transmission to the second node if the minimum delay period has not elapsed since a prior transmission from the first node to the second node.

2. The method of claim 1, further comprising the step of interleaving transmissions to different nodes in the network during the delay of a transmission to the second node by the delaying means.

3. The method of claim 1, wherein the step of determining an estimate of the data handling capability of the second node comprises the step of detecting over an interval the number of negative acknowledgment responses received from the second node in response to attempted transmissions from the first node to the second node.

4. The method of claim 3, wherein the step of determining an estimate of the data handling capability of the second node further comprises the steps of:

detecting over the interval the number of attempted transmissions from the first node to the second node; and determining a rate of negative acknowledgement responses from the number of negative acknowledgement responses and the number of attempted transmissions.

5. The method of claim 4, wherein the step of defining a minimum delay period comprises the step of specifying different minimum delay periods for different rates of negative acknowledgement responses.

6. The method of claim 4, wherein the step of defining a minimum delay period comprises the step of specifying different minimum delay periods for different ranges of negative acknowledgement response rates.

7. The method of claim 4, wherein the step of defining a minimum delay period comprises the steps of:

specifying an initial minimum delay period corresponding to rates of negative acknowledgement responses within a first range; and specifying incremental and decremental changes in the minimum delay period corresponding respectively to increases and decreases in the rate of negative acknowledgement responses outside of the first range.

8. An arbitration circuit for a bus interface unit, comprising:

packet transmission circuitry electrically coupled to a network communication bus by which said bus interface unit arbitrates for control of said network communication bus and transmits packets on said network communication bus when control of said network communication bus has been gained by said bus interface unit, said packet transmission circuitry including circuitry for detecting negative acknowledgement responses received by said bus interface unit in response to attempted packet transmissions by said bus interface unit;

memory circuitry for storing an estimate of data handling capability for each of a plurality of nodes on said network communication bus; and dedicated information processing circuitry, electrically coupled to said memory circuitry and said packet transmission circuitry, for determining said estimate of data handling capability for each of said plurality of nodes as a function of a rate of said negative acknowledgment signals received from each of said plurality of nodes, said estimate for each of said plurality of nodes being determined independently of any source of information directly indicative of total data handling load on said plurality of nodes caused by transmissions from said bus interface unit and said plurality of nodes, and for selectively delaying sequential packet transmissions by said bus interface unit to a particular one of said plurality of nodes as a function of said estimate for that particular node.

9. The apparatus of claim 8, further comprising memory circuitry electrically coupled to said dedicated information processing circuitry for queueing packets ready for transmission by said bus interface unit, and counter circuitry electrically coupled to said dedicated information processing circuitry for sequentially identifying nodes to which queued packets may be transmitted by said bus interface unit during a delay of sequential packet transmissions to said particular node.

10. A network interface apparatus for connecting a first node to a network communication bus, comprising:

carrier sense circuitry for generating a carrier sense signal indicating whether a carrier is present on the network communication bus;

signal sampling circuitry electrically coupled to said carrier sense circuitry;

first memory circuitry electrically coupled to said signal sampling circuitry for receiving signals measuring transmission activity on the network communication bus based on samples of said carrier sense signal;

second memory circuitry for storing programmed signals indicating threshold values associated with said transmission activity;

third memory circuitry for storing an estimate of data handling capability for each of a plurality of other nodes;

packet transmission circuitry electrically coupled to said network communication bus and said carrier sense circuitry; and dedicated information processing circuitry, electrically coupled to said first, second and third memory circuitry and said packet transmission circuitry, for executing a packet scheduling routine which causes said packet transmission circuitry to attempt to gain control of said network communication bus by arbitration when a packet is scheduled for transmission, a bus bandwidth scheduling routine for selectively delaying sequential arbitration attempts by said packet transmission circuitry as a function of said measures and said threshold values, and a node-specific throttling routine for determining said estimate of data handling capability for each of said plurality of other nodes as a function of a rate of said negative acknowledgment signals received from each of said plurality of other nodes, said estimate for each of said plurality of other nodes being determined independently of any source of information directly indicative of total data handling load on said plurality of other nodes caused by transmissions from said first node and said plurality of other nodes, and for selectively delaying sequential packet transmissions to a particular one of said plurality of other nodes as a function of said estimate for said particular node.

11. The apparatus of claim 10, wherein said packet transmission circuitry maintains continous control of said network communication bus while said node-specific throttling routine selectively delays sequential packet transmissions.

12. The apparatus of claim 11, further comprising fourth memory circuitry electrically coupled to said dedicated information processing circuitry for queueing packets ready for transmission by said first node, and counter circuitry electrically coupled to said dedicated information processing circuitry for sequentially identifying nodes to which queued packets may be transmitted by said first node during a delay of sequential packet transmissions to said particular node.

* * * * *